United States Patent [19]

Tadokoro et al.

[11] Patent Number: 5,061,714
[45] Date of Patent: Oct. 29, 1991

[54] ISOQUINOLINE COMPOSITION FOR THE TREATMENT OF GLAUCOMA OR OCULAR HYPERTENSION

[75] Inventors: Toyohiro Tadokoro; Kiyoshi Sato; Shigeki Hatakeyama; Shigeo Kawase; Masao Ueno, all of Saitama, Japan

[73] Assignee: Nisshin Flour Milling Co., Ltd., Tokyo, Japan

[21] Appl. No.: 664,335

[22] Filed: Mar. 4, 1991

Related U.S. Application Data

[62] Division of Ser. No. 495,386, Mar. 16, 1990.

[30] Foreign Application Priority Data

Mar. 28, 1989 [JP] Japan .................................. 1-73866
Sep. 20, 1989 [JP] Japan .................................. 1-242303

[51] Int. Cl.$^5$ ...................... A61K 31/47; C07D 217/24
[52] U.S. Cl. ...................................... 514/309; 546/142
[58] Field of Search .......................................... 514/309

[56] References Cited

U.S. PATENT DOCUMENTS 4,129,565 12/1978 Fukushima et al. ................. 546/142
4,517,365 5/1985 Kayoma et al. ...................... 546/142
4,659,833 4/1987 Takahashi et al. ................... 546/142

FOREIGN PATENT DOCUMENTS 41673 11/1978 Japan .
55512 11/1988 Japan .

OTHER PUBLICATIONS

Fukushima, et al., "Chemical Abstracts", vol. 86, 1977, Col. 86:189739n.

*Primary Examiner*—C. Warren Ivy
*Assistant Examiner*—James H. Turnipseed
*Attorney, Agent, or Firm*—Abelman, Frayne & Schwab

[57] ABSTRACT

The use of isoquinoline derivatives for the treatment of glaucoma or ocular hypertension. The isoquinoline derivatives are of formula I

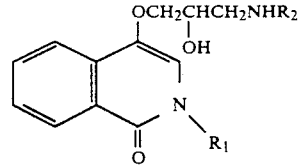

wherein $R_1$ is a hydrogen or a $C_1$–$C_6$ alkyl group and $R_2$ is a $C_1$–$C_6$ alkyl group. The stability of the isoquinoline derivatives when used in the form of a solution is improved by incorporating therein compounds having a phenolic hydroxyl group and/or glycols serving as a stabilizer.

5 Claims, No Drawings

ISOQUINOLINE COMPOSITION FOR THE TREATMENT OF GLAUCOMA OR OCULAR HYPERTENSION

This is a division of application Ser. No. 495,386, filed on Mar. 16, 1990.

BACKGROUND OF THE INVENTION

1. Field of the Invention

This invention is concerned with the use of isoquinoline derivatives for the treatment of glaucoma or ocular hypertension. More particularly, the invention relates to ophthalmological compositions containing an active amount of these isoquinoline derivatives or the pharmaceutically acceptable salts thereof.

2. Description of the Prior Art

Glaucoma is an ocular disorder that causes functional or organic disturbances in the eyes due to continuous or repeated increase in intraocular pressure. The treatment of glaucoma is required to reduce an intra ocular pressure to the normal level in order to maintain optic functions.

Pilocarpine eye drops have been used extensively for the treatment of glaucoma. It is known however that pilocarpine eye drops not only reduce an intraocular pressure but also act on musculi sphincter pupillae and cilia thereby causing side effects such as darkness feeling due to miosis, conjunctival congestion and accommodative injection. Such side effects may invite very serious dangers in operation particularly to persons engaging in transportation. In the case of an elderly patient with cataract, miosis will result in an increased visual disorder. These problems have encouraged development of drugs for the treatment of glaucoma to be substituted for pilocarpine eye drops.

Epinephrine eye drops being a product of such needs are also associated with side effects such as conjunctival congestion, pain at the eyebrow and allergic blepharoconjunctivitis. The eye drops sometimes bring about increased intraocular pressure due to mydriasis and are rarely used. In addition, drugs such as surface-anesthetic agents, pschotropic agents, etc. have been attempted for clinical use in the treatment of glaucoma but none of them is put in practice.

Recently β-receptor blockers have become promising in this field, and timolol maleate, carteolol hydrochloride and befunolol hydrochloride are commercially available as drugs for the treatment of glaucoma.

In view of such situations, we have investigated further medicinal use of isoquinoline derivatives having β-adrenergic blocking activity as disclosed in Japanese Patent Publications No. 41673/1978 and No. 55512/1988 and found that they possess an intraocular pressure reduction activity and are useful for the treatment of glaucoma and ocular hypertension. As far as we know, it has not been reported that the isoquinoline derivatives as disclosed above have been used for the treatment of glaucoma or ocular hypertension.

DETAILED DESCRIPTION OF THE INVENTION

The present invention thus relates to a compound of formula I

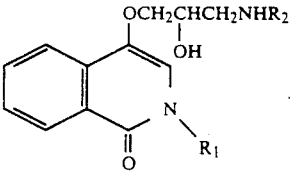

wherein $R_1$ is a hydrogen atom or a $C_1$–$C_6$ alkyl group and $R_2$ is a $C_1$–$C_6$ alkyl group and the pharmaceutically acceptable salt to be used for the treatment of glaucoma or ocular hypertension.

In the above formula I, the $C_1$–$C_6$ alkyl group includes preferably straight or branched alkyl groups of 1–4 carbon atoms, e.g., methyl, ethyl, propyl, isopropyl, butyl and tert.-butyl. The pharmaceutically acceptable salts include the salts of the compounds with inorganic or organic acids such as hydrochloric, sulfuric, nitric, hydrobromic, oxalic, maleic, fumaric, citric, tartaric or malic acid.

Representative examples of the compounds of formula I are illustrated below.

4-(3-tert.-Butylamino-2-hydroxypropoxy)-1-isoquinolinone, 4-(3-tert.-Butylamino-2-hydroxypropoxy)-2-methyl-1-isoquinolinone, 4-(3-Isopropylamino-2-hydroxypropoxy)-1-isoquinolinone, 4-(3-Isopropylamino-2-hydroxypropoxy)-2-methyl-1-isoquinolinone, 4-(3-Ethylamino-2-hydroxypropoxy)-1-isoquinolinone, 4-(3-Ethylamino-2-hydroxypropoxy)-2-methyl-1-isoquinolinone and 4-(3-Ethylamino-2-hydroxypropoxy)-2-ethyl-1isoquinolinone.

Further, the invention relates to compositions for the treatment of glaucoma or ocular hypertension which comprises as an active ingredient an effective intraocular pressure reducing amount of a compound of formula I

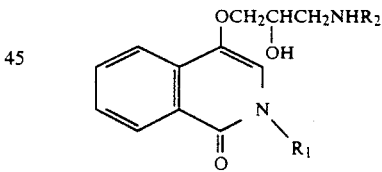

wherein $R_1$ is a hydrogen atom or a $C_1$–$C_6$ alkyl group and $R_2$ is a $C_1$–$C_6$ alkyl group and the pharmaceutically acceptable salt. Preferred concentration of the active ingredient in the composition is usually in the range of about 0.1 to 5% by weight.

The compositions of the invention are prepared in unit dosage form by blending the compounds of formula I or the pharmaceutically acceptable salts thereof with an ophthalmologically compatible carrier. As the unit dosage form may be employed any of various forms as needed such as eye ointments, eye drops for topical administration, and tablets, granules, injections for systemic administration. The mode of use in the form of eye drops is preferred in terms of such effects as rapid onset, easiness in administration and smaller dose.

The compositions of the invention are preferably administered at a daily dose for the active ingredient in adults usually between 0.005 and 2.5 mg and more preferably between 0.025 and 1.0 mg divided in one to several doses, although the dosage is not particularly limited.

The dosage forms in the present invention can be prepared by blending the active ingredients with ophthalmologically compatible carriers and if required shaping the blend. In cases where the dosage form is in such a form as eye ointments, eye drops or injections, further sterilization treatment is required. The carriers may appropriately be selected depending upon the dosage forms. In preparing the eye ointments, conventional carriers such as emulsifiable, water-soluble or suspensible carriers may be employed. They include e.g., white petrolatum, plastibase 50 W, purified lanolin and liquid paraffin. In preparing the eye drops, sterilized distilled water may be used as a carrier.

In the preparation of the dosage forms, ophthalmologically compatible additives may be further employed which include a solubilizing adjuvant, a stabilizing aid, a viscosity increasing agent, a buffer, an antioxidant, a preservative and the like. The solubilizing adjuvants may include sodium carboxymethyl cellulose, polyoxyethylene glycol ethers such as polyoxyethylene lauryl ether and polyoxyethylene oleyl ether, polyethylene glycol higher fatty acid esters such as polyethylene glycol monolaurate and polyethylene glycol monooleate and polyoxyethylene fatty acid esters such as polyoxyethylene sorbitan monolaurate and polyoxyethylene sorbitan monooleate.

The stabilizing aid may include, sodium benzoate, ethanol, benzyl alcohol, D-mannitol, glucose or the like. The viscosity increasing agents may include methyl cellulose, hydroxypropylmethyl cellulose, polyvinyl alcohol, carboxymethyl cellulose, hydroxyethyl cellulose, polyvinyl pyrrolidone, glycerin, carboxyvinyl polymers or the like. The buffers may include sodium dihydrogen phosphate, sodium monohydrogen phosphate, potassium hydrogen phosphate, boric acid, sodium borate, citric acid, sodium citrate, tartaric acid, sodium tartarate and sodium acetate. The antioxidants may include sodium bisulfite, sodium sulfite, sodium thiosulfite, sodium pyrosulfite, oxyquinoline sulfate and ascorbic acid. The preservatives may include chlorobutanol, benzethonium chloride, benzalkonium chloride, cetylpyridinium chloride, thimerosal and phenethyl alcohol. When the compositions of the invention is in the form of eye drops, it is preferable to prepare eye drops that are isotonic to tears, for which an isotoning agent such as sodium chloride may be added, if required. The eye drops are desirably adjusted to a pH of 5.5 to 9.0, preferably 6.5 to 8.5.

Furthermore, we have found that stability of the above compositions when used in the form of a solution is much improved by incorporating therein at least one of a compound containing a phenolic hydroxyl group and glycols serving as a stabilizer. The present invention thus relates to stabilized compositions for the treatment of glaucoma or ocular hypertension which comprises an effective intraocular pressure reducing amount of a compound of formula I

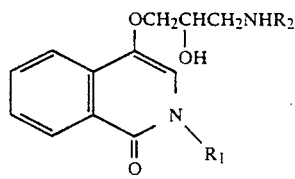

wherein $R_1$ is a hydrogen atom or a $C_1$–$C_6$ alkyl group and $R_2$ is a $C_1$–$C_6$ alkyl group or the pharmaceutically acceptable salt and at least one of a compound of formula II

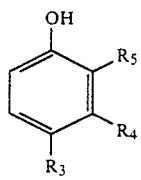

wherein $R_3$, $R_4$ and $R_5$ may be the same or different and each is a hydrogen atom, a halogen atom, a $C_1$–$C_6$ alkyl group, a $C_1$–$C_6$ alkoxy group, a carboxyl group or a $C_1$–$C_6$ alkoxycarbonyl group and a compound of formula III $$HO—[(CH_2)_m—O]_n—H$$

wherein m is an integer of 2 to 4 and n is an integer of 1 to 30.

In the above formula II, the halogen atom includes F, Cl, Br and I, the $C_1$–$C_6$ alkyl group includes preferably straight chain or branched alkyl of 1 to 4 carbon atoms such as methyl, ethyl, propyl. isopropyl, butyl and tert.-butyl, the $C_1$–$C_6$ alkoxy groups include preferably straight chain or branched alkoxy groups of 1 to 4 carbon atoms such as methoxy, ethoxy, propoxy. isopropoxy, butoxy and tert.-butoxy and the $C_1$–$C_6$ alkoxycarbonyl groups include straight-chain or branched alkoxycarbonyl groups in which the alkyl moiety contains preferably 1 to 4 carbon atoms such as methoxycarbonyl, ethoxycarbonyl, propoxycarbonyl isopropoxycarbonyl, butoxycarbonyl and tert.-butoxycarbonyl.

Representative examples of the compounds of formula II include phenol, o-, m- and p-cresols, methoxyphenol, hydroxybenzoic acid, methyl hydroxybenzoate, ethyl hydroxybenzoate, propyl hydroxybenzoate, isopropyl hydroxybenzoate, butyl hydroxybenzoate, isobutyl hydroxybenzoate, butylhydroxyanisol, butylhydroxytoluene, 4-chloro-m-cresol and the like.

Examples of the compounds represented by formula (III) include ethylene glycol, propylene glycol, butylene glycol, polyethylene glycol, polypropylene glycol or the like.

The compounds of formulae II and III as the stabilizer are used either alone or in combination therewith and they can be used in an amount up to the maximum of the solubility in the carrier, usually an amount in the range of 0.02 to 10.00% (w/v) being preferred.

The above stabilized compositions of the present invention are especially advantageous to the use as eye drops, since they exhibit extended storage stability. They can be prepared into a variety of dosage forms in a similar way as described above.

The invention moreover relates to a method for treating glaucoma or ocular hypertension. The method consists in contacting a composition or a stabilized composition as described above with the eye in order to reduce eye pressure and to maintain said pressure on a reduced level. The composition contains about 0.1 to 5% by weight of the active substance, i.e., the compound of formula I. The treatment may advantageously be carried out in that one drop of the composition, corresponding to 0.005-2.5 mg, preferably 0.025-1.0 mg/day for adult may be administered about 1 to 4 times to the patient's eye.

The compositions of the present invention are administered by a variety of routes of administration depending on the unit dosage form. For example, the eye drops are either dropped into the eyes from an appropriate eye dropper or sprayed onto the eye by means of an atomizer. The eye ointments are applied to the eye. The tablets, granules or the like is orally administered, and the injections are administered subcutaneously, intramuscally or intravenously. The expected therapeutic effects can equally be produced by any of the mentioned routes.

The invention is illustrated by means of the following non-limitative examples.

EXAMPLE 1

| | |
|---|---|
| 4-(3-tert-Butylamino-2-hydroxypropoxy)-2-methyl-1-isoquinolinone hydrochloride | 10 mg |
| Benzethonium chloride | 0.1 mg |
| Sodium chloride | 3 mg |
| Sodium dihydrogen phosphate | 5 mg |
| Sodium monohydrogen phosphate.12H$_2$O | 11.8 mg |
| Distilled water | q.s. |
| | Total 1 ml |

A solution of the above-mentioned components in distilled water was subjected to sterile filtration using a suitable filter to prepare eye drops.

EXAMPLE 2

| | |
|---|---|
| 4-(3-tert-Butylamino-2-hydroxypropoxy)-1-isoquinolinone hydrochloride | 20 mg |
| Benzethonium chloride | 0.1 mg |
| Sodium chloride | 3 mg |
| Sodium dihydrogen phosphate | 5 mg |
| Sodium monohydrogen phosphate.12H$_2$O | 11.8 mg |
| Distilled water | q.s. |
| | Total 1 ml |

A solution of the above-mentioned components in distilled water was subjected to sterile filtration using a suitable filter to prepare eye drops.

Efficacy test

Action of the eye drops produced in the above examples on normal intraocular pressure was investigated in male Japanese white rabbits each weighing 2.2-2.9 kg. Intraocular pressure was measured by means of Alcon's pneumatic applanation tonometer (Nippon Alcon Co., Ltd.).

One 15 eye was applied with 100 μl of the drug solution, and changes of the intraocular pressure were measured at time intervals. The intraocular pressure one hour prior to the eye drop application was taken as the preapplication level. A solution with the active agent excluded from the formulation was used as a control. The control and the formulation were evaluated in one and the same rabbit at an off-drug period of one week. The results are shown in Tables 1 and 2 below.

TABLE 1

| | No. of animals | Pre-application | \multicolumn{6}{c}{Intraocular pressure (mmHg)} |
|---|---|---|---|---|---|---|---|---|
| | | | 1 hr. | 2 | 3 | 4 | 5 | 6 |
| Control | 3 | 17.8 | 19.0 | 17.8 | 18.0 | 17.8 | 19.9 | 20.7 |
| Example 1 | 3 | 19.8 | 16.0 | 16.8 | 15.7 | 17.2 | 16.8 | 18.2 |

(Mean value for 3 animals)

TABLE 2

| | No. of animals | Pre-application | \multicolumn{6}{c}{Intraocular pressure (mmHg)} |
|---|---|---|---|---|---|---|---|---|
| | | | 1 hr. | 2 | 3 | 4 | 5 | 6 |
| Control | 3 | 18.9 | 19.2 | 18.0 | 17.6 | 18.5 | 17.8 | 19.0 |
| Example 2 | 3 | 19.1 | 15.2 | 16.0 | 16.6 | 17.3 | 18.1 | 17.9 |

(Mean value for 3 animals)

The results indicate that the eye drops of the invention can achieve remarkable pressure reduction.

Acute toxicity test 4-(3-tert.-Butylamino-2-hydroxypropoxy)-2-methyl-1-isoquinolinone hydrochloride and 4-(3-tert.-butylamino-2-hydroxypropoxy)-1-isoquinolinone hydrochloride, respectively were administered to mice to determine the LD$_{50}$ value. The results are shown in Tables 3 and 4 below.

TABLE 3

| Route of administration | Sex | LD$_{50}$ (mg/kg) |
|---|---|---|
| Oral | Male | 1393 |
| | Female | 1290 |
| Intraperitoneal | Male | 578 |
| | Female | 557 |

TABLE 4

| Route of administration | Sex | LD$_{50}$ (mg/kg) |
|---|---|---|
| Oral | Male | 2810 |
| | Female | 2470 |
| Intraperitoneal | Male | 382 |
| | Female | 367 |

EXAMPLE 3

In an appropriate amount of a 0.2M solution of disodium hydrogen phosphate were dissolved 1.0 g of 4-(3-tert.-butylamino-2-hydroxypropoxy)-2-methyl-1-isoquinolinone hydrochloride (called hereafter "tilisolol hydrochloride") as an active ingredient and 0.1 g of phenol as a stabilizer. A 0.2M solution of sodium dihydrogen phosphate was added as a buffer so as to adjust pH to 7.4, giving a total amount of 100 ml. The resulting solution was sterile filtered through an appropriate filter paper and divided with 5 ml portions into PET vessels for eye dropping. After stored under light shielding in a thermostat at 50° C. for 60 days the solution was analyzed by HPLC for percent of tilisolol hydrochloride retained. Degree of coloration was also examined Stability of the eye drops was compared with reference to the percent of tilisolol hydrochloride retained and the degree of coloration.

EXAMPLES 4–21

The same procedures as in Example 3 were followed except that one or two various stabilizers were used in place of phenol used in Example 3. The content of tilisolol hydrochloride was also changed in Examples 16 and 17.

EXAMPLES 22–24

The same procedures as in Example 3 were followed except that one or two various stabilizers were used in place of phenol used in Example 3, and the stabilizer was dissolved in an appropriate amount of a 0.05M solution of sodium borate (in place of the 0.2M solution of sodium hydrogen phosphate as a buffer) followed by addition of a 0.2M solution of boric acid so as to adjust pH to 7.4 thus giving a total amount of 100 ml.

CONTROL EXAMPLE 1

The same procedure as in Example 3 was followed after preparing a solution of 1.0 g of tilisolol hydrochloride dissolved in distilled water to a total amount of 100 ml. pH was 5.8 at this time.

CONTROL EXAMPLE 2

The same procedure as in Example 3 was followed except that no phenol was contained.

CONTROL EXAMPLE 3

The same procedure as in Example 22 was followed except that no stabilizer was contained.

CONTROL EXAMPLE 4

The same procedure as in Example 16 was followed except that no stabilizer was contained.

CONTROL EXAMPLE 5

The same procedure as in Example 17 was followed except that no stabilizer was contained.

Formulae of the solutions prepared in the above Examples and Control Examples are summarized in Table 5 below.

TABLE 5

| Ex. No. | Tilisolol hydro-chloride (g) | Buffer* | Stabilizer | (g) |
|---|---|---|---|---|
| 3 | 1.0 | P + P | Phenol | 0.1 |
| 4 | " | " | o-Methoxyphenol | 0.12 |
| 5 | " | " | m-Methoxyphenol | 0.12 |
| 6 | " | " | p-Methoxyphenol | 0.12 |
| 7 | " | " | o-Hydroxybenzoic acid | 0.14 |
| 8 | " | " | m-Hydroxybenzoic acid | 0.14 |
| 9 | " | " | p-Hydroxybenzoic acid | 0.14 |
| 10 | " | " | Methyl m-hydroxybenzoate | 0.15 |
| 11 | " | " | Methyl p-hydroxybenzoate | 0.15 |
| 12 | " | " | Methyl p-hydroxybenzoate | 0.05 |
| 13 | " | " | Methyl p-hydroxybenzoate | 0.10 |
| 14 | " | " | Methyl p-hydroxybenzoate | 0.20 |
| 15 | " | " | Methyl p-hydroxybenzoate | 0.25 |
| 16 | 0.5 | " | Methyl p-hydroxybenzoate | 0.15 |
|  |  |  | Propyl p-hydroxybenzoate | 0.05 |
| 17 | 2.0 | " | Methyl p-hydroxybenzoate | 0.15 |
|  |  |  | Propyl p-hydroxybenzoate | 0.05 |
| 18 | 1.0 | " | Methyl p-hydroxybenzoate | 0.15 |
|  |  |  | Propyl p-hydroxybenzoate | 0.05 |
| 19 | " | " | 4-Chloro-m-cresol | 0.14 |
| 20 | " | " | Propylene glycol | 5.0 |
| 21 | " | " | Methyl p-hydroxybenzoate | 0.02 |
|  |  |  | Ethylene glycol | 5.0 |
| 22 | " | B + B | Ethyl p-hydroxybenzoate | 0.14 |

TABLE 5-continued

| Ex. No. | Tilisolol hydro-chloride (g) | Buffer* | Stabilizer | (g) |
|---|---|---|---|---|
| 23 | " | " | Propyl p-hydroxybenzoate | 0.14 |
| 24 | 1.0 | B + B | Methyl p-hydroxybenzoate | 0.26 |
|  |  |  | Ethyl p-hydroxybenzoate | 0.02 |
| Control Example |  |  |  |  |
| 1 | 1.0 | Distilled water | None |  |
| 2 | 1.0 | P + P | None |  |
| 3 | 1.0 | B + B | None |  |
| 4 | 0.5 | P + P | None |  |
| 5 | 2.0 | " | None |  |

*P + P: Prepared by dissolving the stabilizer in a 0.02M solution of disodium hydrogen phosphate followed by addition of a 0.2M solution of sodium dihydrogen phosphate to adjust pH to 7.4.
B + B: Prepared by dissolving the stabilizer in a 0.05M solution of sodium borate followed by addition of a 0.2M solution of boric acid to adjust pH to 7.4.

Each of the solutions prepared in the above Examples and Control Examples was tested for percent of tilisolol hydrochloride retained and degree of coloration. The results are shown in Table 6 below.

TABLE 6

| | Stability of tilisolol hydrochloride in a thermostat at 50° C. after 60 days | |
|---|---|---|
| Example No. | Percent of tilisolol hydrochloride retained (%) | Degree of coloration |
| 3 | 84.85 | + |
| 4 | 76.29 | + + |
| 5 | 95.92 | + |
| 6 | 99.00 | + |
| 7 | 81.82 | + + |
| 8 | 96.97 | + |
| 9 | 100.00 | + |
| 10 | 102.92 | — |
| 11 | 106.12 | — |
| 12 | 84.16 | + |
| 13 | 97.96 | + |
| 14 | 105.10 | — |
| 15 | 106.12 | — |
| 16 | 107.27 | — |
| 17 | 95.05 | + |
| 18 | 102.02 | — |
| 19 | 81.63 | + |
| 20 | 101.05 | — |
| 21 | 103.06 | — |
| 22 | 91.74 | — |
| 23 | 79.38 | + |
| 24 | 93.33 | — |
| Control Example | | |
| 1 | 0.00 | + + + + |
| 2 | 53.06 | + + + |
| 3 | 0.00 | + + + + |
| 4 | 53.33 | + + + |
| 5 | 32.94 | + + + |

+ + + +: Markedly colored
+ + +: Considerably colored
+ +: Fairly colored
+: Slightly colored
—: Not colored The above results indicate that the eye drops of the invention are much improved in stability as compared with those in the Control Examples.

Efficacy test

Action of the eye drops (produced in the above Examples and stored for 60 days in a thermostat at 50° C.) on intraocular pressure increase caused by loading with water or glucose was investigated in male Japanese white rabbits each weighing 2.2-3.8 kg. Intraocular pressure was measured by means of Alcon's pneumatic applanation tonometer (Nippon Alcon Co., Ltd.).

Action on Intraocular Pressure Increase Caused by Loading with Water

To an eye was applied 100 μl of the eye drops of Example 18. Thirty minutes later tap water warmed to 37° C. was orally administered by means of a rubber catheter at a dose of 50 ml per kg body weight. Intraocular pressure changes after administration of the water were measured at time intervals.

For Control Example 6, the same measurements were made using a solution in which tilisolol hydrochloride was omitted from the solution of Example 18. Control Example 6 and Example 18 were evaluated in the same rabbits after an off-drug period of one week. The results are shown in Table 7 below.

Action on Intraocular Pressure Increase Caused by Loading with Glucose

To an eye was applied 100 μl of the eye drops of Example 20. Fifty minutes later a 5% glucose solution was administered via the auricle vein within 60 sec. at a dose of 15 ml per kg body weight. Intraocular pressure changes were measured at time intervals after administration of the glucose solution.

For Control Example 7, the same measurements were made using a solution in which tilisolol hydrochloride was omitted from the solution of Example 20. Control Example 7 and Example 20 were evaluated in the same rabbits after an off-drug period of one week. The results are shown in Table 8 below.

TABLE 7

| | No. of animals | Intraocular pressure change (mmHg) min. | | | | |
|---|---|---|---|---|---|---|
| | | 10 | 20 | 30 | 60 | 180 |
| Control Example 6 | 3 | 5.9 | 8.6 | 8.5 | 1.1 | −1.3 |
| Example 18 | 3 | 1.4 | 5.0 | 4.6 | −1.1 | −1.6 |

(Mean value for 3 animals)

TABLE 8

| | No. of animals | Intraocular pressure change (mmHg) min. | | | | |
|---|---|---|---|---|---|---|
| | | 10 | 20 | 30 | 60 | 180 |
| Control Example 7 | 3 | 6.9 | 4.3 | 3.8 | 1.3 | −0.7 |
| Example 20 | 3 | 0 | −2.0 | −1.6 | −4.1 | −4.9 |

(Mean value for 3 animals)

The above results indicate that the eye drops of the present invention could significantly inhibit the intraocular pressure increase.

EXAMPLE 25

1.0 g of tilisolol hydrochloride and 0.02 g of ethyl p-hydroxybenzoate were dissolved in 0.5 g of a purified water and 2 g of propylene glycol, to which were added 10 g of a purified lanolin. Plastibase 50 W was added to the well blended mixture so as to give a total weight of 100 g. The mixture was filled into a tube to prepare an eye ointment.

EXAMPLES 26-29

The viscosity increasing agents shown in Table 9 below were respectively added to the solution prepared in Example 18 in the indicated amount per 100 ml of the solution to prepare the eye drops. The eye drops were stored under light shielding in a thermostat at 50° C. for 60 days and evaluated for stability with regard to the percent of tilisolol hydrochloride retained and the degree of coloration. The results are shown in Table 9 below.

TABLE 9

| Ex. No. | Viscosity increasing agent (gram per 100 ml of the solution) | Percent of tilisolol hydrochloride retained (%) | Degree of coloration |
|---|---|---|---|
| 26 | Hydroxypropylmethyl cellulose (0.5 g) | 104.3 | — |
| 27 | Polyvinyl pyrrolidone (0.3 g) | 107.1 | — |
| 28 | Carboxyvinyl polymer (0.075 g) | 102.6 | — |
| 29 | Methyl cellulose (1.0 g) | 100.4 | — |

Further, the effect of the viscosity increasing agent added was evaluated with regard to the eye drop prepared in Example 18 and that prepared in Example 26. Each of the eye drops was applied twice with 25 μl portions at intervals of 10 sec. to male Japanese white rabbits each weighing about 3 kg. 25, 60 and 120 minutes after eye dropping, air was injected into the rabbits through ear vein. About 0.3 ml of aqueous humor was taken from the killed rabbits by means of the injector. The concentration of tilisolol in the aqueous humor was determined by HPLC. The results are shown in Table 10 below.

TABLE 10

| | Concentration of tilisolol in aqueous humor (μg/ml) | | | |
|---|---|---|---|---|
| | 0 | 25 min | 60 min | 120 min |
| Eye drop of Example 18 | 0 | 1.15 ± 0.03 | 1.30 ± 0.02 | 0.92 ± 0.16 |
| Eye drop of Example 26 | 0 | 2.25 ± 0.27 | 2.07 ± 0.23 | 1.08 ± 0.26 |

(Mean value for 3 animals)

What is claimed is:

1. A stabilized composition for the treatment of glaucoma or ocular hypertension which comprises an effective intraocular pressure reducing amount of a compound of formula I

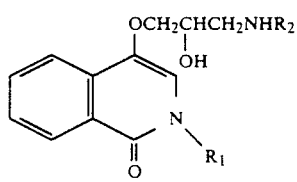

wherein $R_1$ is a hydrogen atom or a $C_1$–$C_6$ alkyl group and $R_2$ is a $C_1$–$C_6$ alkyl group or the pharmaceutically acceptable salt and at least one of a compound of formula II

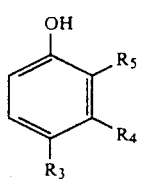

where $R_3$, $R_4$ and $R_5$ may be the same or different and each is a hydrogen atom, a halogen atom, a $C_1$-$C_6$ alkyl group, a $C_1$-$C_6$ alkoxy group, a carboxyl group or a $C_1$-$C_6$ alkoxycarbonyl group and a compound of formula III

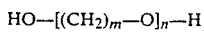

wherein m is an integer of 2–4 and n is an integer of 1 to 30.

2. A composition of claim 1 which further comprises an ophthalmologically compatible carrier and additive.

3. A composition of claim 2 wherein the ophthalmologically compatible carrier is an emulsifiable, water-soluble or suspensible carrier and the ophthalmologically compatible additive is a solubilizing adjuvant, a stabilizing aid, a viscosity increasing agent, a buffer, an antioxidant or a preservative.

4. A composition of claim 1 which is formulated as a dosage form into eye ointments, eye drops, tablets, granules or injections.

5. An eye drop for the treatment of glaucoma or ocular hypertension which comprises an effective intraocular pressure reducing amount of a compound of formula I

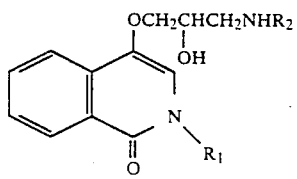

wherein $R_1$ is a hydrogen atom or a $C_1$-$C_6$ alkyl group and $R_2$ is a $C_1$-$C_6$ alkyl group or the pharmaceutically acceptable salt and at least one of a compound of formula II

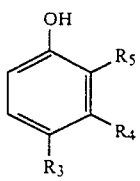

wherein $R_3$, $R_4$ and $R_5$ may be the same or different and each is a hydrogen atom, a halogen atom, a $C_1$-$C_6$ alkyl group, a $C_1$-$C_6$ alkoxy group, a carboxyl group or a $C_1$-$C_6$ alkoxycarbonyl group and a compound of formula III

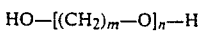

wherein m is an integer of 2 to 4 and n is an integer of 1 to 30.

* * * * *